(12) United States Patent
Liu et al.

(10) Patent No.: US 12,329,509 B1
(45) Date of Patent: Jun. 17, 2025

(54) HIGH-RESOLUTION MAGNETIC RESONANCE FINGERPRINTING METHOD AND DEVICE BASED ON RADIO FREQUENCY ENCODING

(71) Applicant: ZHEJIANG UNIVERSITY, Hangzhou (CN)

(72) Inventors: Huafeng Liu, Hangzhou (CN); Dakun Hu, Hangzhou (CN); Huihui Ye, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/933,677

(22) Filed: Oct. 31, 2024

(30) Foreign Application Priority Data

Mar. 26, 2024 (CN) .......................... 202410350310.X

(51) Int. Cl.
  *G06K 9/00* (2022.01)
  *A61B 5/055* (2006.01)
  (Continued)

(52) U.S. Cl.
  CPC .............. *A61B 5/055* (2013.01); *G01R 33/50* (2013.01); *G01R 33/5608* (2013.01); *G01R 33/5614* (2013.01); *G06T 7/0016* (2013.01); *G06T 11/005* (2013.01); *G06T 11/008* (2013.01); *G06T 2207/10088* (2013.01);
  (Continued)

(58) Field of Classification Search
  CPC .... A61B 5/055; G01R 33/50; G01R 33/5608; G01R 33/5614; G01R 33/4828; G01R 33/5602; G01R 33/4816; G01R 33/561; G06T 7/0016; G06T 11/005; G06T 11/008; G06T 2207/10088; G06T 2207/30016; G06T 2207/30096; G06T 2210/36; G06T 2210/41; G06T 2207/20021; G06T 7/11; G06T 3/40; G06T 3/4038

See application file for complete search history.

(56) References Cited

U.S. PATENT DOCUMENTS 10,598,747 B2 * 3/2020 Gulani ............... G01R 33/4835
10,845,444 B2 * 11/2020 Cohen ................... G01R 33/50
(Continued)

*Primary Examiner* — Atiba O Fitzpatrick
(74) *Attorney, Agent, or Firm* — Jiwen Chen; Joywin IP Law PLLC

(57) ABSTRACT

The present invention is a high-resolution magnetic resonance fingerprinting method based on radio frequency encoding, a device and storage medium, where radio frequency encoding is introduced into MRF, n time evolution signals can be collected by designing and respectively scanning a set of n radio frequency pulse signals, separate time evolution signals representing n sub-slices can be obtained after decoding and calculating according to a encoding process, and then separate quantitative images of the n sub-slices can be obtained through dictionary matching. Compared with conventional MRF, a slice resolution of the quantitative images obtained in the imaging method of the present invention is increased by n times and a signal-to-noise ratio is not reduced. Through a phantom experiment and a human experiment, accuracy of quantitative effect and an effective improvement of the resolution of the present invention are proved, and the present invention can provide higher-resolution quantitative imaging results.

5 Claims, 3 Drawing Sheets

(51) Int. Cl.
*G01R 33/50* (2006.01)
*G01R 33/56* (2006.01)
*G01R 33/561* (2006.01)
*G06T 7/00* (2017.01)
*G06T 11/00* (2006.01)

(52) U.S. Cl.
CPC .............. *G06T 2207/30016* (2013.01); *G06T 2207/30096* (2013.01); *G06T 2210/36* (2013.01); *G06T 2210/41* (2013.01)

(56) References Cited

U.S. PATENT DOCUMENTS

| | | | |
|---|---|---|---|
| 2015/0301142 A1* | 10/2015 | Griswold | G01R 33/4828 |
| | | | 324/309 |
| 2016/0025835 A1* | 1/2016 | Gulani | G01R 33/5635 |
| | | | 600/420 |
| 2016/0061922 A1* | 3/2016 | Grodzki | G01R 33/5608 |
| | | | 324/309 |
| 2016/0091591 A1* | 3/2016 | Grodzki | G01R 33/56509 |
| | | | 324/309 |
| 2018/0203081 A1* | 7/2018 | Cohen | G06N 3/08 |
| 2018/0204045 A1* | 7/2018 | Feiweier | G06V 40/1365 |
| 2018/0372825 A1* | 12/2018 | Griswold | G01R 33/5608 |
| 2019/0353732 A1* | 11/2019 | McGivney | G01R 33/5608 |
| 2020/0341089 A1* | 10/2020 | McGivney | G01R 33/5614 |
| 2020/0341092 A1* | 10/2020 | Jiang | G01R 33/50 |
| 2022/0349972 A1* | 11/2022 | Ma | G01R 33/5601 |

* cited by examiner

HIGH-RESOLUTION MAGNETIC RESONANCE FINGERPRINTING METHOD AND DEVICE BASED ON RADIO FREQUENCY ENCODING

FIELD OF TECHNOLOGY

The present invention belongs to the technical field of magnetic resonance imaging, and in particular to a high-resolution magnetic resonance fingerprinting method based on radio frequency encoding, a device and a storage medium thereof.

BACKGROUND TECHNOLOGY

Magnetic resonance fingerprinting (MRF) is a new quantitative magnetic resonance imaging technology. The MRF adopts a pseudo-random acquisition scheme, and continuously changing acquisition parameters, so that different tissues or materials produce unique signal evolutions. By matching the collected unique signal evolutions with a predefined signal evolution dictionary, a quantitative result of various magnetic parameters of a scanned tissue or material can be obtained at one time, such as T1 (longitudinal relaxation time), and T2 (transverse relaxation time). The quantitative result of these parameters is of great significance and reference value for scientific research and clinical diagnosis and treatment. In addition to an ability to obtain the quantitative result of a plurality of parameters in a single collection, the MRF also has advantages of low sensitivity to a measurement process error and high potential for accelerating collection.

MRF can efficiently obtain the quantitative result of various magnetic parameters of interest of a scanned tissue, but it is restricted by various physical factors. An imaging resolution of conventional 2D MRF can only reach a slice of 3-5 mm. [Badve C, Yu A, Dastmalchian S, et al. M R Fingerprinting of Adult Brain Tumors: Initial Experience [J]. American Journal of Neuroradiology, 2017, 38(3): 492-499], which can not meet needs well in some application scenarios such as detections of some small lesions, segmentation between gray matter and white matter of a brain, and characterization of fine structures such as cerebral cortex. There are some 3D MRF methods [Liao C, Bilgic B, Manhard M K, et al. 3D MR fingerprinting with accelerated stack-of-spirals and hybrid sliding-window and GRAPPA reconstruction [J]. NeuroImage, 2017, 162:13-22] which can achieve a higher slice resolution (about 1 mm), but these methods need to consume a lot of scanning time, and due to a too large volume of data collected by a 3D non-Cartesian trajectory, an image reconstruction process also needs a lot of computing resources and time, which is difficult to adopt in practical application.

Therefore, in order to make the MRF technology adapt to more application scenarios and provide more accurate quantitative results, it will be a practical work to improve the slice resolution of MRF scan image results, that is, to achieve high-resolution quantitative imaging.

SUMMARY OF THE INVENTION

In view of the above, the present invention provides a high-resolution magnetic resonance fingerprinting method based on radio frequency encoding, a device and a storage medium thereof, which can realize high-resolution MRF quantitative imaging by encoding a plurality of radio frequency pulses.

A high-resolution magnetic resonance fingerprinting method based on radio frequency encoding, comprising the following steps:

(1) designing and generating n magnetic resonance fingerprinting sequences with different radio frequency pulses according to required quantitative tissue parameters, wherein the tissue parameters comprise longitudinal relaxation time T1 and transverse relaxation time T2, and n is a natural number greater than 3;

(2) importing the magnetic resonance fingerprinting sequences into a magnetic resonance scanner, and scanning a tissue part to be measured to obtain n sets of original k-space data;

(3) reconstructing all the k-space data to obtain a series of images; and for any pixel, solving corresponding time evolution signals of n continuous sub-slices by combining with the reconstructed n sets of image data;

(4) giving a change range and discretization step sizes of the required quantitative tissue parameters, and establishing a dictionary reflecting a signal timing change based on a Bloch equation; and (5) matching all the time evolution signals of the reconstructed images from step (3) with signals in the dictionary one by one, so as to obtain a specific tissue parameter value for each pixel index, and then obtain quantitative images of the respective tissue parameters at the n sub-slices.

Further, the magnetic resonance fingerprinting sequences designed in step (1) are based on a 2D fast imaging with steady-state precession (FISP) sequence, the n magnetic resonance fingerprinting sequences differ only in the radio frequency pulses, and a corresponding excitation profile of each radio frequency pulse respectively applies a phase modulation of magnitude $\pi$ to a different sub-slice, wherein a thickness of each sub-slice is 1/n of a full thickness of the corresponding excitation profile.

Further, the n time evolution signals of any pixel in step (3) can be regarded as a weighted sum of separate time evolution signals of the n sub-slices, and the independent time evolution signals representing n continuous sub-slices can be solved by combining a weight matrix and a matrix equation determined by a radio frequency encoding method.

Further, the time evolution signals can be regarded as the weighted sum of the separate time evolution signals at the n sub-slices, and is represented by a matrix as:

$$Y_{n \times N \times t} = A_{n \times n} S_{n \times N \times t}$$

wherein $Y_{n \times N \times t}$ represents a combination of n time evolution signals, N represents a total number of pixels in the image, t represents the number of time points in the signal, $S_{n \times N \times t}$ represents the separate signals at the n sub-slices, and $A_{n \times n}$ represents a weighting coefficient matrix determined by a radio frequency encoding mode.

Further, the Bloch equation is used to describe the magnetic resonance fingerprinting sequences designed in step (1), a combination of the required quantitative tissue parameters is given and sequence parameters comprising repetition time (TRs) and flip angles (FAs) are given, which are used as an input of the Bloch equation, and the time evolution signals obtained by the given parameters under the magnetic resonance fingerprinting sequences can be output.

A computer device, comprising a memory and a processor, wherein a computer program is stored in the memory and the processor is used to execute the computer program so as to implement the above high-resolution magnetic resonance fingerprinting method based on radio frequency encoding.

A computer-readable storage medium having a computer program stored thereon, wherein when the computer program is executed by a processor, the above high-resolution magnetic resonance fingerprinting method based on radio frequency encoding is implemented.

The method of the present invention introduces radio frequency encoding into MRF, n time evolution signals can be collected by designing and respectively scanning a set of n radio frequency pulse signals, separate time evolution signals representing n sub-slices can be obtained after decoding and calculating according to a encoding process, and then separate quantitative images of the n sub-slices can be obtained through dictionary matching. Compared with conventional MRF, a slice resolution of the quantitative images obtained in the imaging method of the present invention is increased by n times and a signal-to-noise ratio is not reduced. Through a phantom experiment and a in vivo brain experiment, accuracy of quantitative effect and an effective improvement of the resolution of the present invention are proved, and the present invention can provide higher-resolution quantitative imaging results for tissues of children, small focal areas, gray matter boundaries of brains, etc., which is conducive to scientific research and clinical diagnosis and treatment.

DESCRIPTION OF THE EMBODIMENTS

Figure 1:
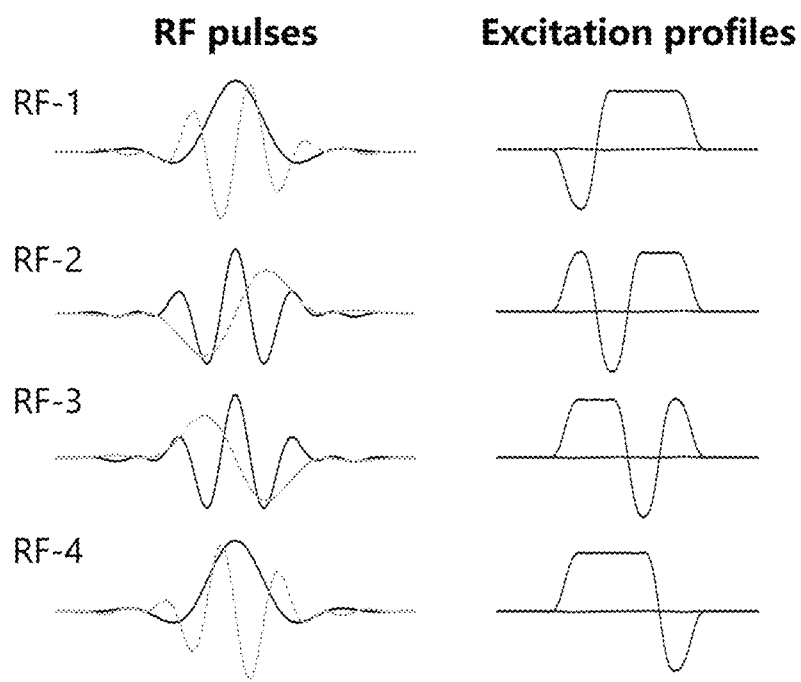
FIG. 1 is a schematic diagram of a group of 4 radio frequency pulse waveforms and their corresponding excitation profiles.

In order to describe the present invention more specifically, technical schemes of the present invention are described in detail in combination with the accompanying drawings and specific embodiments.

A high-resolution magnetic resonance fingerprinting method based on radio frequency encoding of the present invention, comprising the following steps:

(1) designing and generating a group of n magnetic resonance fingerprinting sequences according to required quantitative tissue parameters, wherein the tissue parameters comprise longitudinal relaxation time T1 and transverse relaxation time T2, and the n sequences have different radio frequency pulse signals, and a corresponding excitation profile of each radio frequency pulse applies a phase modulation of magnitude $\pi$ to a different sub-slice.

The magnetic resonance fingerprinting sequences designed by the present invention are based on a 2D FISP sequence. The n sequences are different only in the radio frequency pulses, and the corresponding excitation profile of each radio frequency pulse applies the phase modulation of magnitude $\pi$ to a sub-slice of which thickness is 1/n of a full thickness of the excitation profile.

(2) importing the magnetic resonance fingerprinting sequences into a magnetic resonance scanner, and scanning a tissue part to be measured to obtain n sets of original k-space data.

(3) reconstructing original k-space data to obtain a series of images; for each pixel, solving corresponding time evolution signals of n continuous sub-slices by combining with the reconstructed n sets of data.

The n time evolution signals of each pixel can be regarded as a weighted sum of separate time evolution signals of the n sub-slices, and the independent time evolution signals representing n sub-slices can be solved by combining a weight matrix and a matrix equation determined by a radio frequency encoding method.

(4) giving a range and discretization step sizes of the required quantitative tissue parameters, and establishing a dictionary reflecting a signal timing change based on a Bloch equation.

The Bloch equation describes the magnetic resonance fingerprinting sequences designed in step (1), given a combination of values of the required quantitative tissue parameters and given sequence parameters such as repetition time (TRs) and flip angles (FAs) as an input of the Bloch equation, the time evolution signals obtained by the given parameters under the magnetic resonance fingerprinting sequences can be output.

(5) matching all the time evolution signals of the reconstructed images from step (3) with signals in the dictionary one by one, so as to obtain a specific tissue parameter value for each pixel index, and then obtain quantitative images of the respective tissue parameters at the n sub-slices.

Embodiment Example

The core of the present invention is to encode n radio frequency pulse signals, collect a plurality of groups, use the obtained plurality of groups of time evolution signals to reconstruct separate time evolution signals representing n sub-slices, and then obtain quantitative results with a resolution increased by n times.

A specific procedure of the magnetic resonance fingerprinting method in this embodiment mainly comprises two parts: a design of radio frequency encoding, data collection and processing.

Design of Radio Frequency Encoding

FIG. 1 shows a group of 4 radio frequency pulse waveforms and corresponding excitation profile waveforms, in which 4 radio frequency pulse waveforms are on a left side, dark waveforms are real parts of signals, light waveforms are imaginary parts of the signals, and corresponding excitation profiles of the radio frequency pulses are on a right side. In each excitation profile, a phase modulation of a magnitude $\pi$ is applied to a sub-slice of which thickness is one quarter of an overall profile.

If these 4 radio frequency pulses are used to scan a tissue of interest separately, 4 time evolution signals obtained by direct reconstruction from K-space are denoted as $y_1, y_2, y_3, y_4$, and a complete excitation profile slice is divided into 4 sub-slices of equal thickness. Each signal can be regarded as a different weighted sum of time evolution signals representing the 4 sub-slices, which can be expressed in a matrix form as follows:

$$Y_{4 \times N \times t} = A_{4 \times 4} S_{4 \times N \times t} \quad (1)$$

wherein Y represents a combination of the signals $y_1$, $y_2$, $y_3$, $y_4$, N represents a total number of pixels in the image, t represents the number of time points in the signal, S represents the separate signals at the 4 sub-slices, and A represents a weighting coefficient matrix determined by a radio frequency encoding mode.

According to the matrix equation, we can solve the independent signals representing the 4 sub-slices, and then execute a dictionary matching process for the signals of all sub-slices respectively, that is, obtain quantitative results of the 4 sub-slices. In this way, we can get the quantitative results with a slice resolution increased by 4 times.

Data Collection and Processing

In this embodiment, the data collection and processing are carried out on both a phantom and a human brain based on the radio frequency encoding method.

Firstly, the scan is carried out by using the sequence group of this radio frequency encoding method; a Spiral trajectory and 36 times downsampling are utilized to accelerate the collection process in the scan; by taking a field of view (FOV) as 220 mm, an in-plane resolution as 1 mm×1 mm, and a thickness of an excitation slice as 6 mm, and then quantitative results with a slice resolution of 1.5 mm are obtained; and a single scan takes about 20 seconds, and 4 pieces of k-space data can be obtained from each collection group.

A dictionary is then created, which is a set containing all combinations of possible values of the tissue parameters of interest and corresponding time evolution signal mapping relationships. A basic principle of the magnetic resonance fingerprinting is to match the time evolution signals reconstructed from the k-space with entries in the pre-established dictionary, and the combinations of the parameter values of the interested issue corresponding to the entries with the best match are used as quantitative parameter results of pixels represented by the time evolution signals. In this embodiment, parameter range for the dictionary is T1 (100:20:2000 2100:100:3000 ms), T2 (10:5:15 160:10:200 220:20:300 400:100:2000 ms), and the specific time evolution signals in the dictionary is calculated by a Bloch equation.

Finally, it is signal processing and matching quantization; the image can be obtained by applying two-dimensional inverse Fourier transform to k-space data; and each pixel corresponds to a group of time evolution signals. In this embodiment, each pixel corresponds to 4 time evolution signals. According to formula (1), time evolution signals representing the 4 sub-slices can be solved, and these signals are matched with the dictionary entries for pixels one by one to obtain quantitative results of the T1 and T2 parameters of the 4 sub-slices respectively. An inner product is calculated in sequence when the time evolution signals are matched with the dictionary entries, and an entry with a largest inner product is a matching result.

Figure 2A:
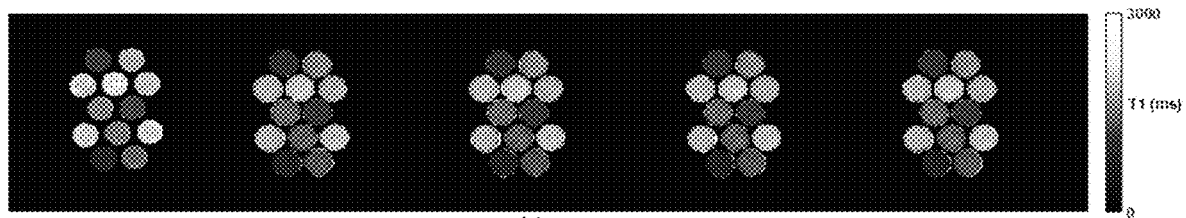
FIG. 2(a) shows gold standard T1 quantitative results of a phantom collected by Multi-TI IR-SE and T1 quantitative results of the phantom collected by a radio frequency encoding method of the present invention.
Figure 2B:
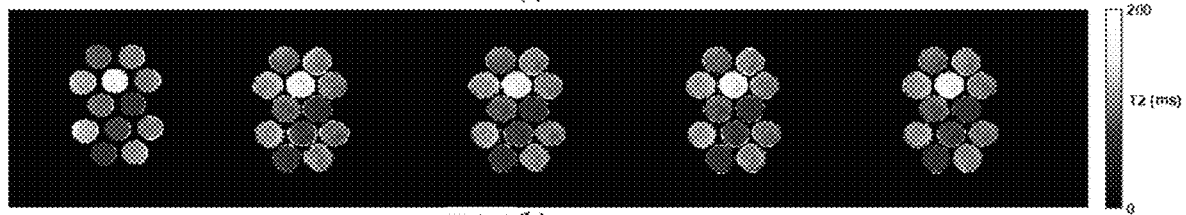
FIG. 2(b) shows gold standard T2 quantitative results of the phantom collected by Multi-TE SE and T2 quantitative results of the phantom collected by the radio frequency encoding method of the present invention.

The leftmost column in FIG. 2(a) shows gold standard T1 quantitative results of the phantom collected by Multi-TI IR-SE and the right four columns show T1 quantitative results of the 4 sub-slices of the phantom obtained by the present invention. The leftmost column in FIG. 2(b) shows gold standard T2 quantitative results of the phantom collected by Multi-TE SE and the right four columns show T2 quantitative results of the 4 sub-slices of the phantom obtained by the present invention. It can be seen that the quantitative results of the phantom of the present invention are highly consistent with the gold standard, and the 4 sub-slices obtained by the present invention have good consistency, which verifies accuracy and consistency of quantitative effects of the method of the present invention.

Figure 2C:
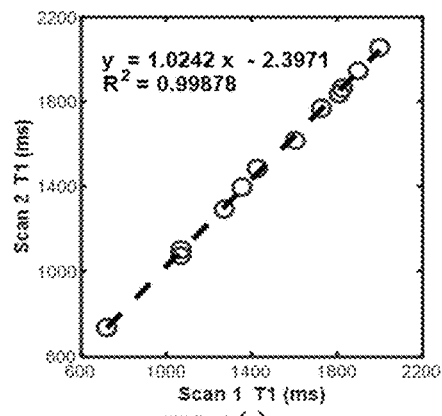
FIG. 2(c) shows a schematic diagram of T1 average quantitative results for the same region of interest ROI in two different scans of the phantom.
Figure 2D:
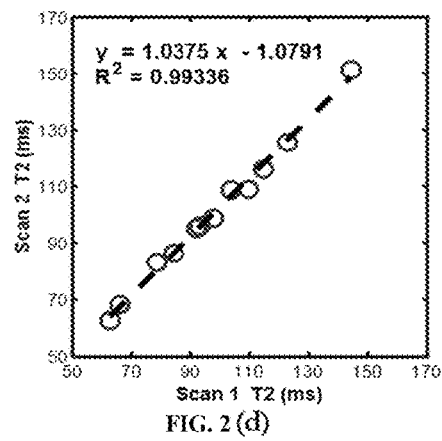
FIG. 2(d) shows a schematic diagram of T2 average quantitative results for the same region of interest ROI in two different scans of the phantom.

FIG. 2(c) and FIG. 2(d) show that horizontal and vertical coordinates of each point respectively represent an average quantitative value of the same area of interest (ROI) in two different scans on the phantom, wherein FIG. 2(c) is the quantitative results of T1, FIG. 2(d) is the quantitative results of T2, and dashed lines are results of linear fitting of all points, indicating that the results of the two scans are stable. It is proved that the method of the present invention has repeatability.

Figure 3:
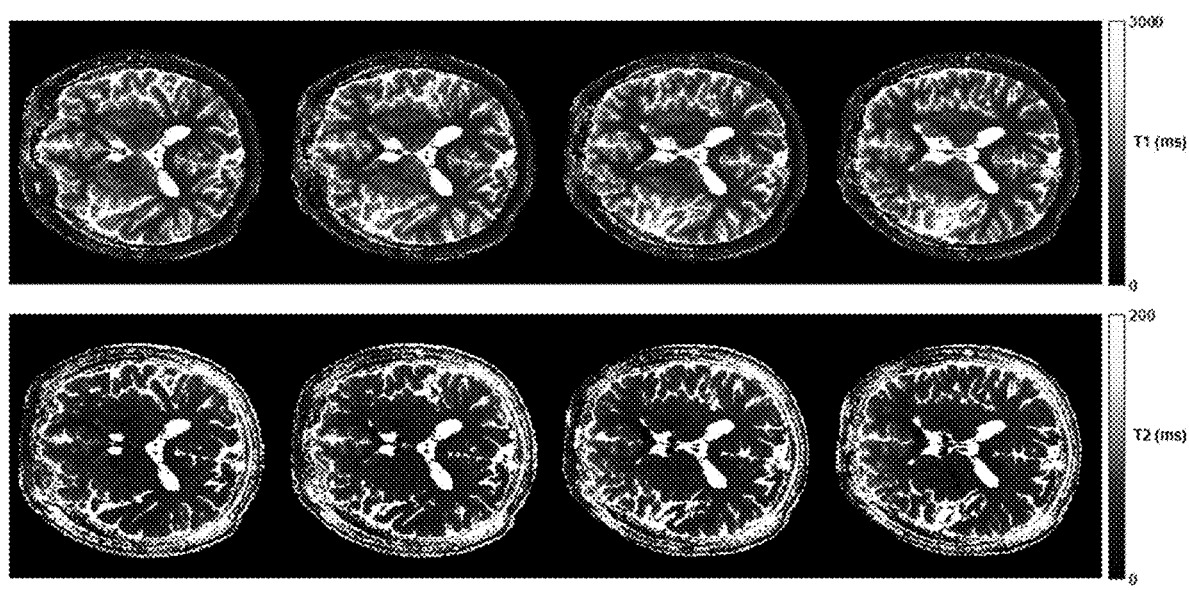
FIG. 3 is a schematic diagram of experimental results of the radio frequency encoding method of the present invention on a human brain.

In FIG. 3, the four columns in the first row show the T1 quantitative results of the 4 sub-slices of a human brain obtained by the present invention, and the four columns in the second row show the T2 quantitative results of the 4 sub-slices of the human brain obtained by the present invention. It can be seen that the quantitative results of the 4 sub-slices of the human brain of the present invention have good continuity and consistency, and subtle structural differences of adjacent slices can be clearly distinguished, which verifies the consistency of quantitative effects of the present invention and an effect of improving the resolution.

The description of embodiments above is intended to facilitate the understanding and application of the present invention by a person skilled in the art, and a person skilled in the art can obviously easily make various modifications to the above embodiments and apply the general principles described herein to other embodiments without creative labor. Therefore, the present invention is not limited to the above embodiments, and the improvements and modifications of the present invention made by a person skilled in the art according to the disclosure of the present invention shall be within the protection scope of the present invention.

What is claimed is:

1. A high-resolution magnetic resonance fingerprinting method based on radio frequency encoding, comprising the following steps:
   (1) designing and generating n magnetic resonance fingerprinting sequences with different radio frequency pulses according to required quantitative tissue parameters, wherein the tissue parameters comprise longitudinal relaxation time T1 and transverse relaxation time T2, and n is a natural number greater than 3;
   wherein the magnetic resonance fingerprinting sequences are based on a 2D FISP sequence, the n magnetic resonance fingerprinting sequences differ only in the radio frequency pulses, and a corresponding excitation profile of each radio frequency pulse respectively applies a phase modulation of magnitude π to a different sub-slice, wherein a thickness of each sub-slice is 1/n of a full thickness of the corresponding excitation profile;
   (2) importing the magnetic resonance fingerprinting sequences into a magnetic resonance scanner, and scanning a tissue part to be measured to obtain n sets of original k-space data;
   (3) reconstructing all the k-space data to obtain a series of images; and for any pixel, solving corresponding time evolution signals of n continuous sub-slices by combining with the reconstructed n pieces of image data;
   wherein the n time evolution signals of any pixel can be regarded as a weighted sum of separate time evolution signals of the n sub-slices, and the independent time evolution signals representing n continuous sub-slices can be solved by combining a weight matrix and a matrix equation determined by a radio frequency encoding method;

(4) giving a range and discretization step sizes of the required quantitative tissue parameters, and establishing a dictionary reflecting a signal evolution based on a Bloch equation; and (5) matching all the time evolution signals of the reconstructed images from step (3) with signals in the dictionary one by one, so as to obtain a specific tissue parameter value for each pixel index, and then obtain quantitative images of the respective tissue parameters at the n sub-slices.

2. The high-resolution magnetic resonance fingerprinting method according to claim 1, wherein the time evolution signals can be regarded as the weighted sum of the separate time evolution signals at the n sub-slices, and is represented by a matrix as:

$$Y_{n \times N \times t} = A_{n \times n} S_{n \times N \times t}$$

wherein $Y_{n \times N \times t}$ represents a combination of n time evolution signals, N represents a total number of pixels in the image, t represents the number of time points in the signal, $S_{n \times N \times t}$ represents the separate signals at the n sub-slices, and $A_{n \times n}$ represents a weighting coefficient matrix determined by a radio frequency encoding mode.

3. The high-resolution magnetic resonance fingerprinting method according to claim 1, wherein the Bloch equation is used to describe the magnetic resonance fingerprinting sequences designed in step (1), a combination of the required quantitative tissue parameters is given and sequence parameters comprising TRs and FAs are given, which are used as an input of the Bloch equation, and the time evolution signals obtained by the given parameters under the magnetic resonance fingerprinting sequences can be output.

4. A computer device, comprising a memory and a processor, wherein a computer program is stored in the memory and the processor is used to execute the computer program so as to implement the high-resolution magnetic resonance fingerprinting method according to claim 1.

5. A non-transitory computer-readable storage medium having a computer program stored thereon, wherein when the computer program is executed by a processor, the high-resolution magnetic resonance fingerprinting method according to claim 1 is implemented.

* * * * *